(12) United States Patent
Hodak

(10) Patent No.: US 11,460,120 B2
(45) Date of Patent: *Oct. 4, 2022

(54) ONE-WAY CHECK VALVE

(71) Applicant: Michael L. Hodak, Venetia, PA (US)

(72) Inventor: Michael L. Hodak, Venetia, PA (US)

(73) Assignee: Michael L. Hodak, Venetia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/229,920

(22) Filed: Apr. 14, 2021

(65) Prior Publication Data

US 2021/0231225 A1   Jul. 29, 2021

Related U.S. Application Data

(63) Continuation of application No. 16/071,268, filed on Jul. 19, 2018, now Pat. No. 11,002,376.

(60) Provisional application No. 62/354,496, filed on Jun. 24, 2016, provisional application No. 62/316,093, filed on Mar. 31, 2016, provisional application No. 62/281,926, filed on Jan. 22, 2016.

(51) Int. Cl.
*F16K 15/06* (2006.01)
*F16K 15/14* (2006.01)
*F16K 27/02* (2006.01)

(52) U.S. Cl.
CPC ........ *F16K 15/148* (2013.01); *F16K 27/0209* (2013.01)

(58) Field of Classification Search
CPC ............................ F16K 15/148; F16K 27/0209
See application file for complete search history.

(56) References Cited

U.S. PATENT DOCUMENTS

| 2,756,106 A | | 7/1956 | Schenk | |
| 2,996,077 A | * | 8/1961 | Taggert | F16K 15/044 137/537 |
| 3,957,114 A | | 5/1976 | Streich | |
| 4,334,537 A | * | 6/1982 | Peterson | A61F 5/4405 137/541 |
| 4,429,856 A | * | 2/1984 | Jackson | F16L 37/38 251/149.1 |
| 4,681,139 A | | 7/1987 | Falconer | |
| 4,712,619 A | | 12/1987 | Stepp et al. | |
| 4,723,694 A | | 2/1988 | Sykes | |
| 4,766,927 A | | 8/1988 | Conatser | |
| 5,168,586 A | | 12/1992 | Small | |

(Continued)

FOREIGN PATENT DOCUMENTS

CA   2308865 A1   11/2000
EP   0236083 A1   9/1987

*Primary Examiner* — P. Macade Nichols
(74) *Attorney, Agent, or Firm* — The Webb Law Firm

(57) ABSTRACT

A sealing assembly for controlling a flow of fluid through a fluid line has a housing having a first end opposite a second end with a hollow interior extending therebetween and an elastically resilient plug disposed within the hollow interior of the housing. The plug has a body engagable with a seat within the housing and a tension member having a first end connected to the body and a second end connected to the housing. The tension member is pre-loaded in tension to urge the body of the plug against the seat to seal the hollow interior of the housing. The body is movable away from the seat when the plug is acted upon by a fluid pressure greater than a pre-load force of the tension member.

19 Claims, 12 Drawing Sheets

(56) References Cited

U.S. PATENT DOCUMENTS

| | | | |
|---|---|---|---|
| 5,743,872 A | 4/1998 | Kelly | |
| 6,257,503 B1 | 7/2001 | Baudin | |
| 6,510,277 B1 | 1/2003 | Dongo | |
| 11,002,376 B2 * | 5/2021 | Hodak | F16K 15/06 |
| 2003/0051757 A1 | 3/2003 | Roth et al. | |
| 2003/0116199 A1 | 6/2003 | Schroeder et al. | |
| 2011/0276035 A1 | 11/2011 | Fangrow et al. | |

* cited by examiner

ONE-WAY CHECK VALVE

CROSS-REFERENCE TO RELATED APPLICATIONS

This application is a continuation of U.S. application Ser. No. 16/071,268, filed Jan. 19, 2017, which claims priority to U.S. Provisional Application No. 62/281,926, filed on Jan. 22, 2016 and entitled "Winterizing Plug for Fitting on Swimming Pool"; U.S. Provisional Application No. 62/316,093, filed on Mar. 31, 2016 and entitled "One-Way Check Valve"; and U.S. Provisional Application No. 62/354,496, filed on Jun. 24, 2016 and entitled "One-Way Check Valve", the disclosures of which are incorporated herein in their entirety.

BACKGROUND OF THE INVENTION

Field of the Invention

The present invention relates generally to a sealing apparatus for closing off a fluid line to prevent water from entering the fluid line, and in particular, to a one-way check valve for closing of the fluid line, such as the fluid line of a swimming pool.

Brief Description of the Prior Art

It is common to employ one or more fluid lines in the sidewalls of swimming pools, spas, hot tubs, and the like to permit surface water to be drawn off by a pump, to be filtered at a remote location and then optionally heated, and returned to the pool through one or more return ports. For example, the pump may have one or more inlet lines for drawing water from the pool into the pump and one or more water outlet lines for pumping water into the pool after it has been filtered and/or heated. The inlet and/or outlet lines (hereinafter referred to as "fluid line" or "fluid lines") may run underground between the pool and the pump located at a remote location from the pool. When the pool is closed, for example during the winter season, it is sometimes desirable to maintain a lower level of water in the pool. Even if completely drained, the water level in the pool tends to naturally rise due to rainwater and melting snow, such that the water level oftentimes rises to a level of the fluid line opening or above. In such cases, it is necessary to close off the fluid line to prevent backflow of water through the fluid line conduit to the filtration, pump equipment, and/or heater so as to prevent damage to the fluid line, filtration equipment, and/or heater due to freezing during the cold winter months.

One common way of closing off the fluid line is to employ a threaded plug that threadably mates with the terminal end of the fluid line. The plug is threadably secured with the fluid line to seal the conduit communicating with the pump and filtration equipment. These prior devices may lose their effectiveness due to weathering of the seal material, and also may require special retrofitting of the fluid line opening member to enable a threaded connection. Accordingly, there is a need in the art for an improved sealing apparatus for closing off a fluid line to prevent water from entering the fluid line when the pool is closed for the season. There is also a need in the art for an improved sealing apparatus configured for use as a one-way check valve in various other environments, including, without limitation, the food service industry, the petrochemical industry, and various other industrial processes.

SUMMARY OF THE INVENTION

The present sealing apparatus, in accordance with one preferred and non-limiting embodiment or aspect of the present disclosure, is directed to a sealing apparatus for closing off a fluid line to prevent water from entering the fluid line when the pool, spa, hot tub, or the like is closed for the season. The sealing apparatus may be used with a fluid line on a swimming pool and may be designed dimensionally to fit common circularly-shaped fluid line openings of various sizes.

In accordance with one preferred and non-limiting embodiment or aspect of the present disclosure, a sealing assembly for controlling a flow of fluid through a fluid line may have a housing having a first end opposite a second end with a hollow interior extending therebetween and an elastically resilient plug disposed within the hollow interior of the housing. The plug may have a body engagable with a seat within the housing and a tension member having a first end connected to the body and a second end connected to the housing. The tension member may be pre-loaded in tension to urge the body of the plug against the seat to seal the hollow interior of the housing. The body may be movable away from the seat when the plug is acted upon by a fluid pressure greater than a pre-load force of the tension member.

In accordance with other preferred and non-limiting embodiments or aspects of the present disclosure, the housing may have a flange that protrudes radially outward from the housing at the first end of the housing. The flange may have one or more gripping members to facilitate handling of the housing during connection of the housing to the fluid line. The flange may have one or more threads to threadably interface with at least a portion of the fluid line to removably connect the housing to the fluid line. At least one of the body of the plug and the seat may have a conical shape. The seat may have a liner, wherein the body of the plug directly engages the liner. The plug may be made from an elastomeric material. The second end of the tension member may have a bulbous tail that is received in a slot between a pair of substantially parallel bars extending across the hollow interior of the housing. The plug may have at least one gripping element protruding from at least one of the body and the bulbous tail. The plug may have a core and a cover at least partially surrounding the core. The core is hollow or solid, and may completely envelop the core.

In accordance with other preferred and non-limiting embodiments or aspects of the present disclosure, a one-way check valve may have a housing having a hollow interior and an elastomeric plug sealing the hollow interior of the housing. The plug may have a body engaged with a seat within the housing and a pre-loaded tension member having a first end connected to the body and a second end connected to the housing. The plug may be movable away from the seat when the plug is acted upon by a fluid pressure greater than a pre-load force of the tension member.

In accordance with other preferred and non-limiting embodiments or aspects of the present disclosure, the housing may have a flange that protrudes radially outward from the housing at the first end of the housing. The flange may have one or more gripping members to facilitate handling of the housing during connection of the housing to the fluid line. The flange may have one or more threads to threadably interface with at least a portion of the fluid line to removably connect the housing to the fluid line. At least one of the body of the plug and the seat may have a conical shape. The second end of the tension member may have a bulbous tail that is received in a slot between a pair of substantially parallel bars extending across the hollow interior of the housing. The plug may have a core and a cover at least partially surrounding the core.

In accordance with other preferred and non-limiting embodiments or aspects of the present disclosure, a sealing assembly for controlling a flow of fluid through a fluid line may have a housing having a first end opposite a second end with a hollow interior extending therebetween, and an elastomeric plug disposed within the hollow interior. The plug may have a body engagable with a seat within the housing and an elastic compression member having a first end connected to the body and a second end connected to the housing. The compression member may be pre-loaded in compression to urge the body of the plug against the seat to seal the hollow interior of the housing. The body may be movable away from the seat when the plug is acted upon by a fluid pressure greater than a pre-load force of the compression member.

In accordance with other preferred and non-limiting embodiments or aspects of the present disclosure, the sealing apparatus may be defined by one or more of the following clauses:

Clause 1. A sealing assembly for controlling a flow of fluid through a fluid line, the sealing assembly comprising:
a housing having a first end opposite a second end with a hollow interior extending therebetween;
an elastically resilient plug disposed within the hollow interior, the plug having a body engagable with a seat within the housing and a tension member having a first end connected to the body and a second end connected to the housing,
wherein the tension member is pre-loaded in tension to urge the body of the plug against the seat to seal the hollow interior of the housing, and
wherein the body is movable away from the seat when the plug is acted upon by a fluid pressure greater than a pre-load force of the tension member.

Clause 2. The sealing assembly of clause 1, wherein the housing comprises a flange that protrudes radially outward from the housing at the first end of the housing.

Clause 3. The sealing assembly of clause 2, wherein the flange comprises one or more gripping members to facilitate handling of the housing during connection of the housing to the fluid line.

Clause 4. The sealing assembly of clause 2 or clause 3, wherein the flange comprises one or more threads to threadably interface with at least a portion of the fluid line to removably connect the housing to the fluid line.

Clause 5. The sealing assembly of any of clauses 1-4, wherein at least one of the body of the plug and the seat have a conical shape.

Clause 6. The sealing assembly of any of clauses 1-5, wherein the seat comprises a liner and wherein the body of the plug directly engages the liner.

Clause 7. The sealing assembly of any of clauses 1-6, wherein the plug is made from an elastomeric material.

Clause 8. The sealing assembly of any of clauses 1-7, wherein the second end of the tension member has a bulbous tail that is received in a slot between a pair of substantially parallel bars extending across the hollow interior of the housing.

Clause 9. The sealing assembly of clause 8, wherein the plug has at least one gripping element protruding from at least one of the body and the bulbous tail.

Clause 10. The sealing assembly of any of clauses 1-9, wherein the plug comprises a core and a cover at least partially surrounding the core.

Clause 11. The sealing assembly of clause 10, wherein the core is hollow or solid.

Clause 12. The sealing assembly of clause 10 or clause 11, wherein the cover completely envelops the core.

Clause 13. A one-way check valve comprising:
a housing having a hollow interior;
an elastomeric plug sealing the hollow interior of the housing, the plug having a body engaged with a seat within the housing and a pre-loaded tension member having a first end connected to the body and a second end connected to the housing,
wherein the plug is movable away from the seat when the plug is acted upon by a fluid pressure greater than a pre-load force of the tension member.

Clause 14. The one-way check valve of clause 13, wherein the housing comprises a flange that protrudes radially outward from the housing at the first end of the housing.

Clause 15. The one-way check valve of clause 14, wherein the flange comprises one or more gripping members to facilitate handling of the housing during connection of the housing to the fluid line.

Clause 16. The one-way check valve of clause 14 or clause 15, wherein the flange comprises one or more threads to threadably interface with at least a portion of the fluid line to removably connect the housing to the fluid line.

Clause 17. The one-way check valve of any of clauses 13-16, wherein at least one of the body of the plug and the seat have a conical shape.

Clause 18. The one-way check valve of any of clauses 13-17, wherein the second end of the tension member has a bulbous tail that is received in a slot between a pair of substantially parallel bars extending across the hollow interior of the housing.

Clause 19. The one-way check valve of any of clauses 13-18, wherein the plug comprises a core and a cover at least partially surrounding the core.

Clause 20. A sealing assembly for controlling a flow of fluid through a fluid line, the sealing assembly comprising:
a housing having a first end opposite a second end with a hollow interior extending therebetween;
an elastomeric plug disposed within the hollow interior, the plug having a body engagable with a seat within the housing and an elastic compression member having a first end connected to the body and a second end connected to the housing,
wherein the compression member is pre-loaded in compression to urge the body of the plug against the seat to seal the hollow interior of the housing, and
wherein the body is movable away from the seat when the plug is acted upon by a fluid pressure greater than a pre-load force of the compression member.

These and other features and characteristics of the improved sealing apparatus, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only.

BRIEF DESCRIPTION OF THE DRAWINGS

In FIGS. 1-16B, the same characters represent the same components unless otherwise indicated.

DETAILED DESCRIPTION OF INVENTION

Figure 1:
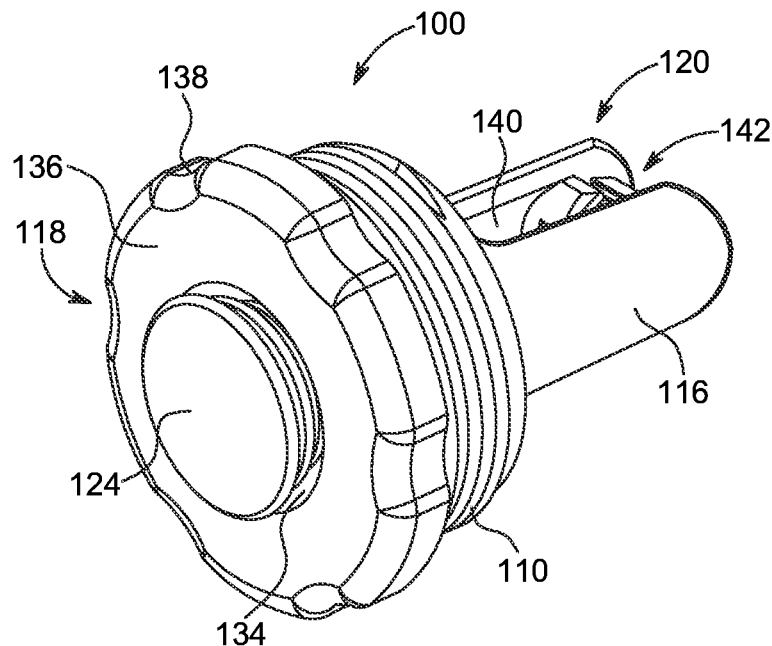
FIG. 1 is a front perspective view of a sealing apparatus of one preferred and non-limiting embodiment or aspect of the present disclosure showing the sealing apparatus in an open position.

As used herein, the singular form of "a", "an", and "the" includes plural referents unless the context clearly dictates otherwise.

As used herein, spatial or directional terms, such as "left", "right", "up", "down", "inner", "outer", "above", "below", and the like, relate to various features as depicted in the drawing figures. However, it is to be understood that various alternative orientations can be assumed and, accordingly, such terms are not to be considered as limiting.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, the term "substantially parallel" means a relative angle as between two objects (if extended to theoretical intersection), such as elongated objects and including reference lines, that is from 0° to 5°, or from 0° to 3°, or from 0° to 2°, or from 0° to 1°, or from 0° to 0.5°, or from 0° to 0.25°, or from 0° to 0.1°, inclusive of the recited values.

All documents, such as but not limited to issued patents and patent applications, referred to herein, and unless otherwise indicated, are to be considered to be "incorporated by reference" in their entirety.

Figure 2:
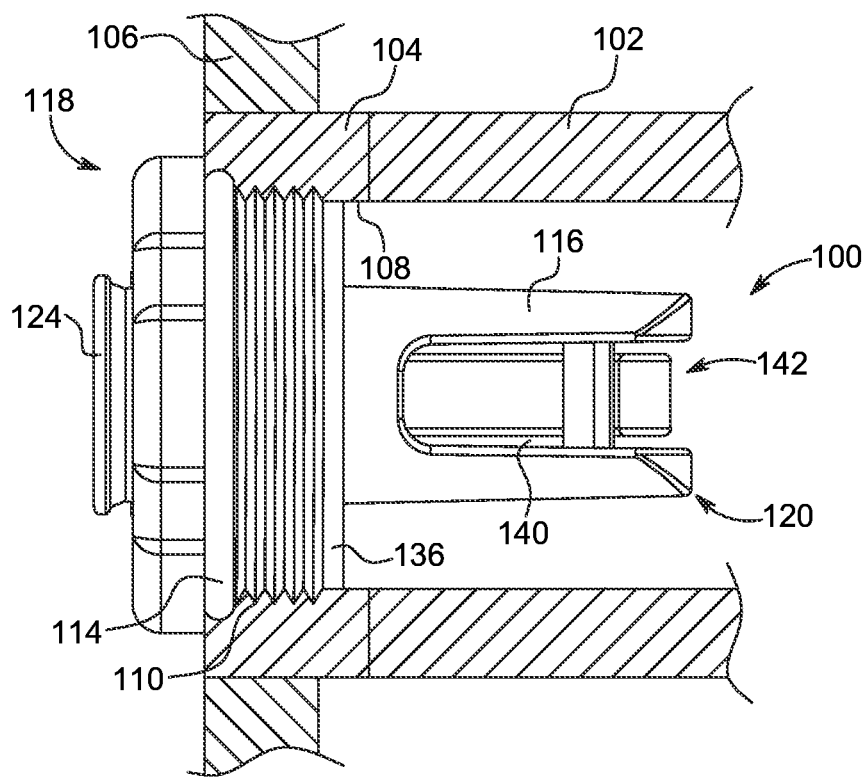
FIG. 2 is a top view of the sealing apparatus shown in FIG. 1 showing the sealing apparatus in an open position.

With reference to FIGS. 1-2, a sealing apparatus 100 is configured for use with a fluid line 102 (shown in FIG. 2) of a pool, spa, hot tub, or the like. The sealing apparatus 100 is configured to close off the fluid line 102 to prevent water from entering the fluid line 102. In one aspect, the sealing apparatus 100 may be connected to a fitting 104 (shown in FIG. 2) provided on a wall 106 of the pool, spa, hot tub, or the like. The fitting 104 is typically provided at the terminal end of the fluid line 102. The fitting 104 may have a front fascia that conceals an opening in the wall 106 and a central opening 108 that removably or non-removably connects with the fluid line 102. In some aspects, at least one of the fluid line 102 and the fitting 104 may be made from a plastic material, such as ABS plastic. One or more adapters (not shown) may be disposed between the fluid line 102 and the fitting 104.

With continued reference to FIGS. 1-2, the sealing apparatus 100 is configured to be removably connected to at least one of the fluid line 102 and the fitting 104. In one preferred and non-limiting embodiment, the sealing apparatus 100 may removably connect to the fitting 104 by one or more external threads 110 that threadably interface with the one or more internal threads 112 on the fitting 104. One of ordinary skill in the art will readily appreciate that various other connection mechanisms may be provided to removably connect the sealing apparatus 100 with the fitting 104. A seal, such as an O-ring 114, may be provided at an interface between the sealing apparatus 100 and the fitting 104 to seal against water intrusion between these components. In some examples, the O-ring 114 may be formed as a separate component that is subsequently installed around a flange 136 at the first end 118 of the housing 116. In other examples, the O-ring 114 may be monolithically formed with the flange at the first end 118 of the housing 116, such as by overmolding. In this manner, the O-ring 114 and the housing 116 are formed as a single, unitary piece. In various examples, the O-ring 114 may be formed from a thermoplastic elastomer material.

With reference to FIGS. 3A-3D, the sealing apparatus 100 generally has a housing 116 that is configured for connecting with at least a portion of the fitting 104 and/or the fluid line 102. In some aspects, the housing 116 has one or more external threads 110 that threadably interface with the internal threads 112 on the fitting 104. The housing 116 has a generally circular cross-section with a hollow interior between a first end 118 and a second end 120 extending along a longitudinal axis 122. The housing 116 receives a plug 124 to seal the housing interior between the first end 118 and the second end 120.

With continued reference to FIGS. 3A-3D, the housing 116 may narrow from the first end 118 to the second end 120 such that a cross-sectional diameter at the first end 118 is larger than that of the second end 120. A conical portion 132 is provided between the first end 118 and the second end 120 along the longitudinal axis 122. An interior of the conical portion 132 defines a seat 134 against which the plug 124 interfaces when the plug 124 is in a closed position. In some examples, a plug liner (not shown) may be provided such that the plug 124 interfaces directly with the plug liner instead of the seat 134. The plug liner may be formed from an elastically resilient material, such as an elastomer, including, but not limited to rubber. The plug liner may have a substantially conical shape that corresponds to the shape of the conical portion 132 of the housing 116. The plug liner may be removably or non-removably connected to the housing 116. The plug liner may be a coating that is deposited on the seat 134 to improve the sealing characteristics of the seat 134.

With continued reference to FIGS. 3A-3D, the first end 118 of the housing 116 may have a flange 136 that protrudes radially outward from the body of the housing 116. The flange 136 may have one or more gripping members 138 (shown in FIG. 1) to facilitate handling of the housing 116 as the housing 116 is rotated to connect the housing 116 with the fitting 104 and/or the fluid line 102. The O-ring 114 may abut against the flange 136 such that the O-ring 114 is compressed between the flange 136 and the fitting 104 when the sealing assembly 100 is installed.

With continued reference to FIGS. 3A-3D, the second end 120 of the housing 116 may have a generally cylindrical shape with a recess 140 formed at the terminal portion of the second end 120. The recess 140 extends through the sidewall of the housing 116 in a direction substantially perpendicular to a direction of the longitudinal axis 122 into the body of the housing 116. In some aspects, the recess 140 may have an open end 142. In some aspects, a pair of recesses 140 extends into the sidewall of the housing 116 such that the recesses 140 are diametrically opposed to one another.

The first end 118, the second end 120, the conical portion 132, and the recess 140 may be formed as a uniform, monolithic structure. In some aspects, the entire housing 116 may be formed from a plastic material, such as ABS plastic.

Figure 3A:
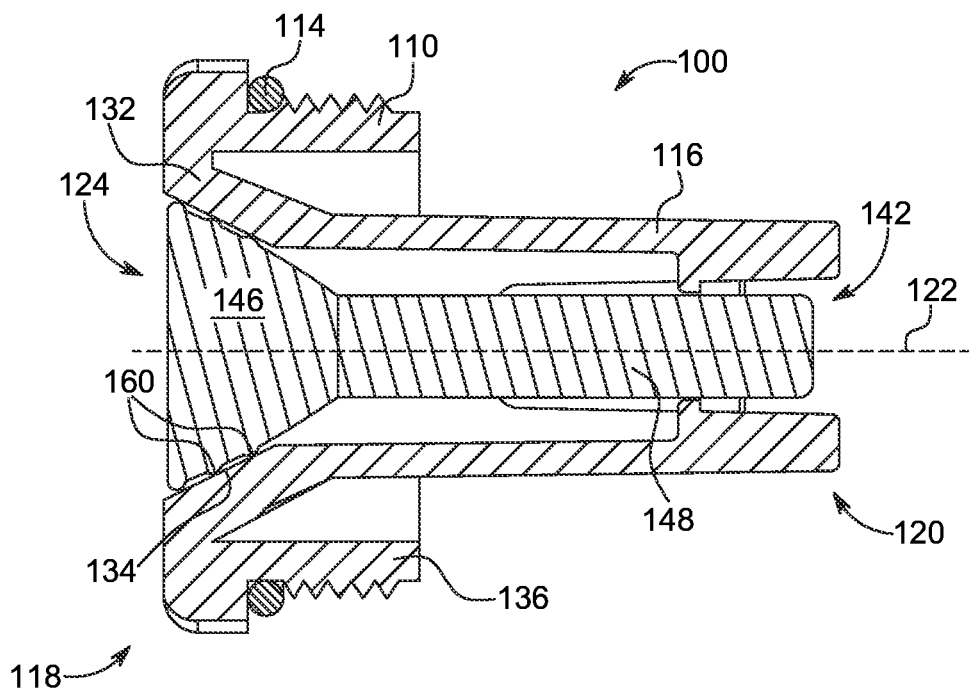
FIG. 3A is a cross-sectional top view of the sealing apparatus shown in FIG. 2 taken along a longitudinal centerline, showing a plug in a closed position.
Figure 3B:
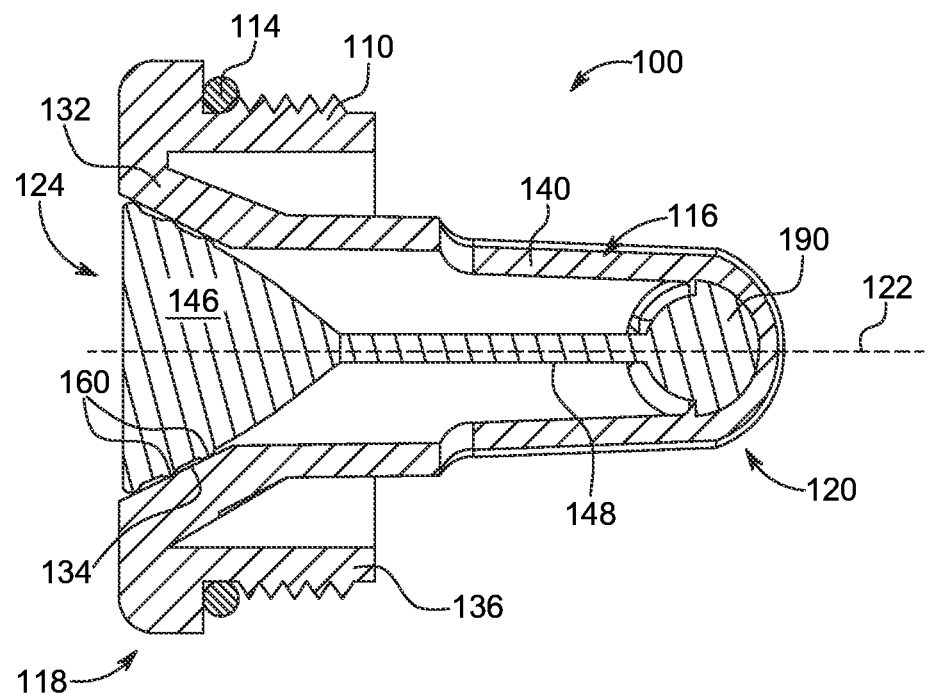
FIG. 3B is a cross-sectional side view of the sealing apparatus shown in FIG. 2 taken along a longitudinal centerline, showing a plug in a closed position.
Figure 3C:
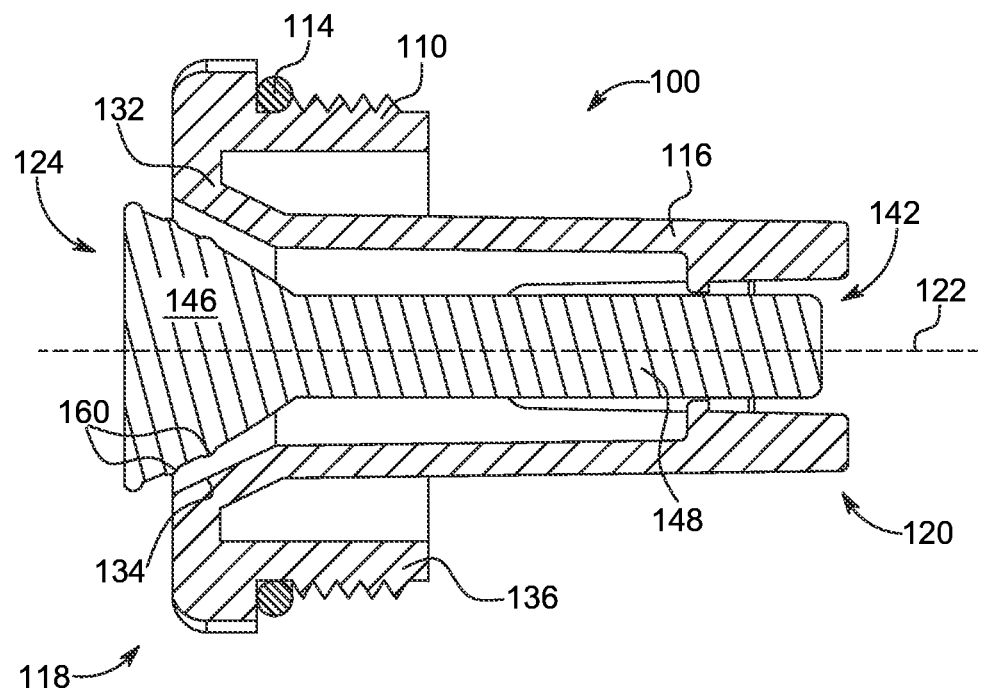
FIG. 3C is a cross-sectional top view of the sealing apparatus shown in FIG. 2 taken along a longitudinal centerline, showing a plug in an open position.
Figure 3D:
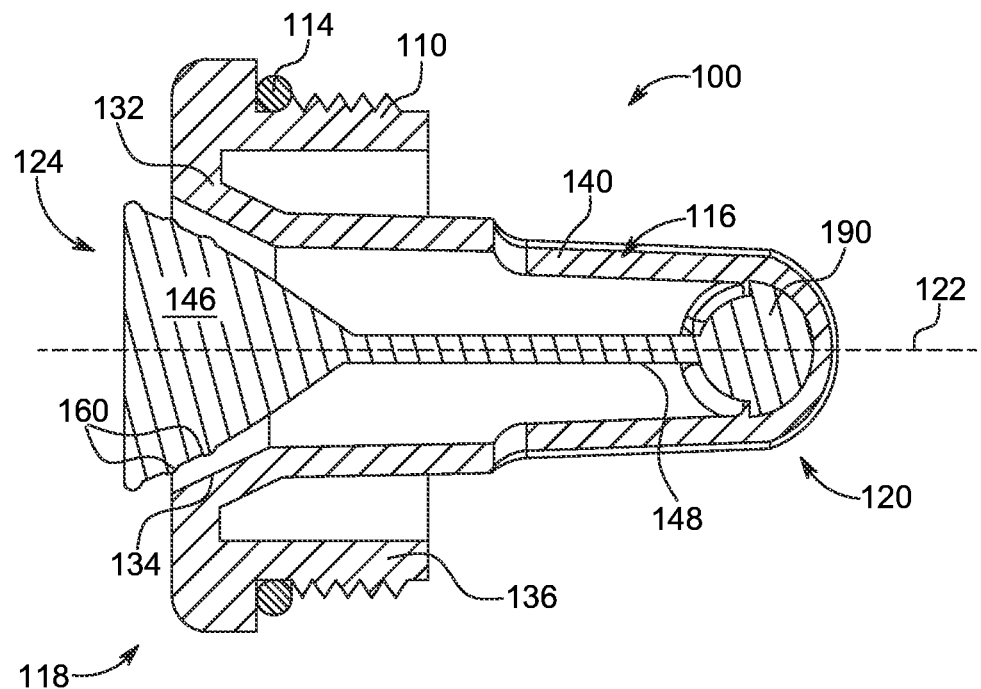
FIG. 3D is a cross-sectional side view of the sealing apparatus shown in FIG. 2 taken along a longitudinal centerline, showing a plug in an open position.
Figure 4A:
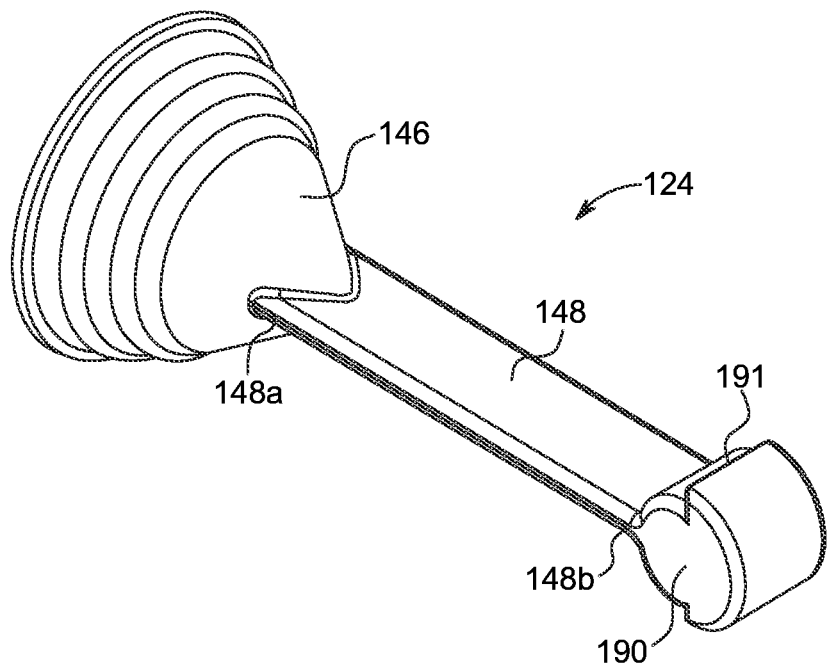
FIG. 4A is a rear perspective view of a plug of the sealing apparatus shown in FIGS. 3A-3B.
Figure 4B:
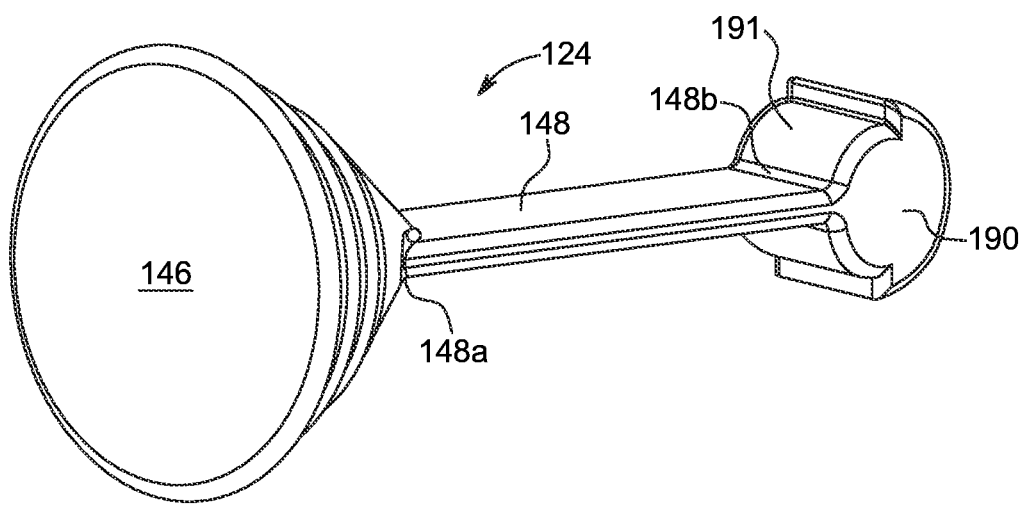
FIG. 4B is a front perspective view of the plug shown in FIG. 4A.

With reference to FIGS. 4A-4B, and with continued reference to FIGS. 3A-3D, the plug 124 is formed as a resiliently elastic body that is inserted into the interior of the housing 116 for sealably interfacing with the seat 134. The plug 124 is movable between a first, closed position (FIGS. 3A-3B), where the plug 124 seals the interior of the housing 116 and prevents fluid from passing therethrough, and a second, open position, where the plug 124 is disengaged from the seat 134 to allow fluid to flow through the housing 116 (shown in FIGS. 3C-3D). In various aspects, the plug 124 may be made from an elastomeric material, such as rubber. The composition of the elastomeric material of the plug 124 may be formulated to be chemically resistant to a variety of fluids, such as water, oil, hydraulic fluid, various gases, and any other liquid or gas. The plug 124 has a substantially conical body 146 and a tension member 148 extending from the body 146. The shape of the body 146 desirably corresponds to the shape of the seat 134 such that the plug 124 may be in surface-to-surface contact with the seat 134 when the plug 124 is in the closed position, as discussed herein.

With continued reference to FIGS. 4A-4B, the body 146 of the plug 124 has one or more sealing elements 160. In some aspects, the one or more sealing elements 160 may be formed as one or more sealing rings that extend around the circumference of the body 146 of the plug 124. The one or more sealing elements 160 may extend continuously or discontinuously around the circumference of the body 146 of the plug 124. The one or more sealing elements 160 may be spaced apart longitudinally at equal or unequal intervals. In some aspects, the one or more sealing elements 160 may be monolithically formed with the body 146 of the plug 124. In other aspects, the one or more sealing elements 160 may be formed separately and connected to the body 146. For example, the one or more sealing elements 160 may be fitted into a circumferential groove formed on the body 146. The one or more sealing elements 160 are configured to engage the seat 134 on the housing 116 such that a water-tight seal is formed around the circumference of the plug 124 at the interface between the one or more sealing elements 160 and the seat 134 on the housing 116.

With continued reference to FIGS. 4A-4B, the tension member 148 has a first end 148a connected to the body 146 of the plug 124 and a second end 148b extending from the first end 148a along a longitudinal axis of the body 146 of the plug 124. The second end 148b terminates in a bulbous tail 190, at least a portion of which extends radially outward relative to a longitudinal length of the tension member 148. In some aspects, the tail 190 may be substantially cylindrical and be configured to engage a retaining mechanism on the housing 116, as described herein. The plug 124 is configured to be installed in the interior of the housing 116 (shown in FIG. 3B) such that the body 146 is seated against the conical portion of the housing 116 and the second end 148b of the tension member 148 is connected to the housing 116 by way of the tail 190. The plug 124 may be pre-loaded such that the plug 124 is biased in a normally closed position due to the resiliently elastic properties of the tension member 148. In this manner, a watertight seal is provided at the interface between the plug 124 and the housing 116 to prevent water from flowing back into the fluid line 102 through the housing 116.

Figure 5:
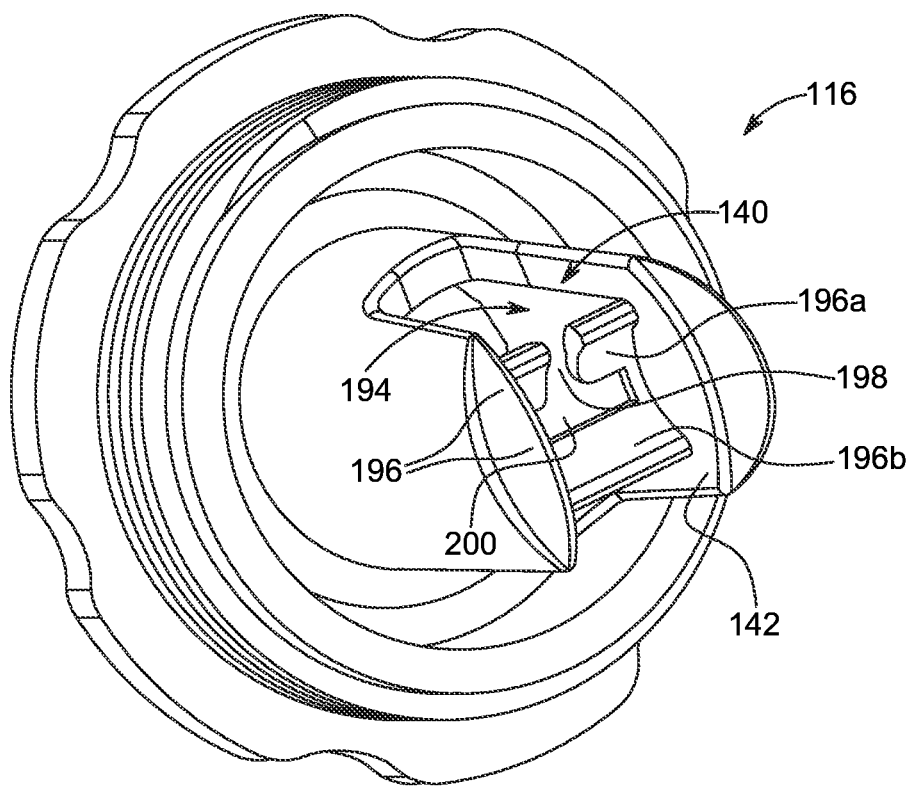
FIG. 5 is a rear perspective view of a housing of the sealing apparatus shown in FIG. 1.

With reference to FIG. 5, the housing has a slot 194 for receiving the tail 190 of the plug 124 (shown in FIG. 3B). In some examples, the slot 194 is defined by a pair of substantially parallel bars 196 that extend across a space between opposing sides of the inner sidewall of the housing 116 in a direction substantially perpendicular to a longitudinal axis of the housing 116. The bars 196 may be shaped to correspond to the shape of the tail 190. For example, the bars 196 may have a substantially arcuate shape to define a semi-circular cavity for receiving the tail 190. The tail 190 and the bars 196 may be shaped to have a smooth transition therebetween. In this manner, the tail 190 and the bars 196 together define an optimized surface with hydromechanical properties that allow high flow rates around the plug 124. In addition, the shape of the tail 190 and the bars 196 prevents vibration of the plug 124 due to fluid flow and/or the formation of bubbles in fluid flow (cavitation).

The bars 196 may be positioned axially such that the tension member 148 must be pulled in a distal direction to allow the tail 190 to be inserted between the bars 196 through a slit 198 formed in one or both of the bars 196. In some examples, a first portion of the tail 190 is received between the bars 196 while a second portion of the tail 190 extends radially outward relative to the bars 196 to allow the user to grip the tail 190 during installation and removal of the plug 124. In some examples, the tail 190 may have a recess 191 that engages the bars 196. The slit 198 may extend through at least one of the bars 196 such that it bisects the bar 196 into two portions 196a, 196b separated by a space 200. The space 200 is desirably at least slightly wider than a narrowest width of the tension member 148. The tension member 148 may be inserted through the space 200 when installing or removing the plug 124 on or from the housing 116.

In some aspects, the plug 124 may have one or more stabilizing elements (not shown) to help stabilize the plug 124 as fluid flows around the body 146 when the sealing apparatus 100 is in an open position. The one or more stabilizing elements may be configured to hydrodynamically balance the plug 124 in fluid flow in order to prevent fluttering of the plug 124 due to uneven hydrodynamic forces on the plug 124. In various aspects, the one or more stabilizing elements may be formed as ribs, wings, protrusions, or other features that protrude radially outward from the plug 124 and/or extend radially inward into the plug 124.

Referring again to FIGS. 3A-3B, the plug 124 is configured to be installed in the interior of the housing 116 such that the body 146 is seated against the conical portion 132 of the housing 116 and the tension member 148 is connected to the slot 194 by way of the tail 190. In some aspects, the plug 124 may be shorter than a distance between the seat 134 and the slot 194 such that at least a portion of the plug 124 is stretched when the plug 124 is installed between the seat 134 and the slot 194. In this manner, the tension member 148 is pre-loaded with a force that urges the body 146 against the seat 134. The tension member 148 may have a smaller cross-section relative to the body 146 of the plug 124 such that the tension member 148 is stretched when the plug 124 is installed between the seat 134 and the recess 140. In some aspects, the entire plug 124 may deform elastically when the plug 124 is installed between the seat 134 and the recess 140 of the housing 116. The elastic force stored in the plug 124, such as the elastic force in the tension member 148, urges the plug 124 against the seat 134. The tension member 148 thus functions similar to a bungee cord that is stretched to have a pre-loaded elastic restoring force. In this manner, a watertight seal is provided at the interface between the plug 124 and the housing 116 to prevent water from flowing back into the fluid line 102 through the housing 116. The hydraulic force of the water acting on the face of the plug 124 further urges the plug 124 against the seat 134.

Figure 14:
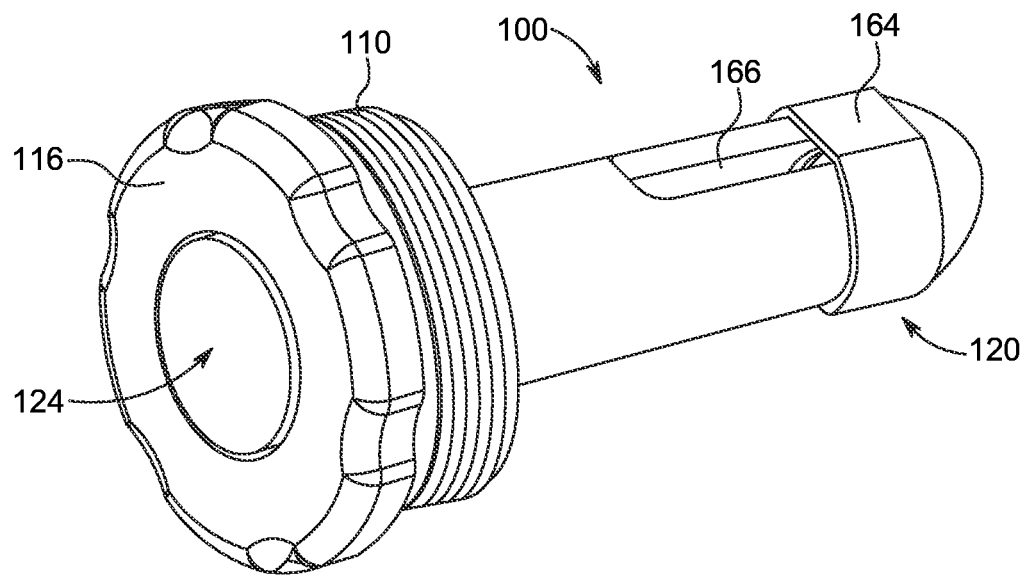
FIG. 14 is a front perspective view of a sealing apparatus of another preferred and non-limiting embodiment or aspect of the present disclosure.
Figure 15:
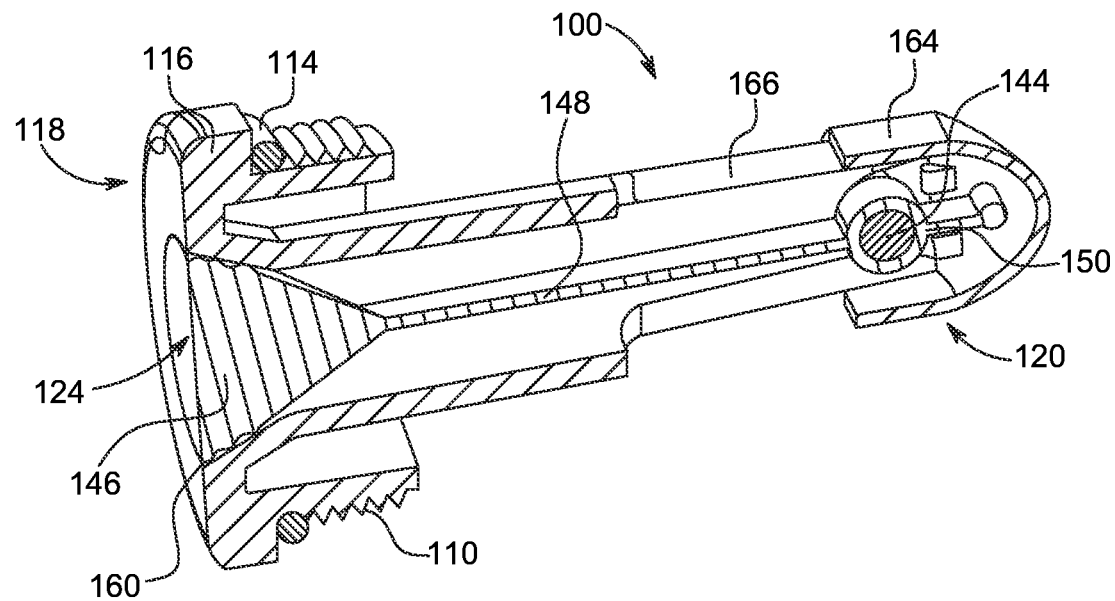
FIG. 15 is a perspective cross-sectional view of the sealing apparatus shown in FIG. 14.

In some examples, such as shown in FIGS. 14-15, a closure member 164 may be provided at the second end 120 of the housing 116. The closure member 164 is configured to fit around the second end 120 of the housing 116 such that the closure member 164 envelops the second end 120. The housing 116 has at least one pocket 166 that extends longitudinally such that the closure member 164 covers at least a portion of the pocket 166. The closure member 164 may be configured as a cup-shaped element that extends around a pin 144 and a receiver 150. In some aspects, the closure member 164 may have a stop element that is configured to engage at least a portion of the housing 116 and/or the pin 144. In use, the closure member 164 prevents the plug 124 from being disconnected from the housing 116 due to any fluttering of the plug 124 as a result of pressure fluctuations in fluid flow through the housing 116. In addition, the closure member 164 may act as a recoil compensator to prevent the plug 124 from being disconnected from the housing 116 during sudden changes in fluid pressure that force the plug 124 to be withdrawn toward the distal end under the restoring elastic force of the tension member 148. Fluid may flow around the housing 116 and through at least one pocket 166 before flowing past the plug 124.

To install the plug 124 on the housing 116, the tail 190 and the tension member 148 are inserted through a front opening on the housing 116 until the body 146 engages the seat 134. The tail 190 is then pulled rearwardly past the bars 196, thereby tensioning the tension member 148, which is inserted between the bars 196 through the slit 198. The tail 190 can then be released, which causes the tail 190 to engage the bars 196 and be retained between the bars 196. The tension member 148 remains in a tensioned state even after the tail 190 engages the bars 196 in order to maintain the body 146 of the plug 124 in a sealed state against the seat 134. To remove the plug 124 from the housing 116, the tail 190 can be pulled rearwardly, thereby disengaging the tail 190 from contact with the bars 196. The tension member 148 can then be pulled through the slit 198, such as by twisting the tension member 148 to align its narrowest dimension with the slit 198. After passing the tension member 148 through the slit 198, the plug 124 can be pulled through the front opening on the housing 116.

Having described the structure of the sealing assembly 100 in accordance with various aspects, a method of operation of the sealing assembly 100 will now be described with reference to FIGS. 3A-3D. The following discussion focuses on the installation and operation of the sealing assembly 100 on a return line of a swimming pool pump (not shown). However, the same or similar installation and operating procedure may be followed in various other installations of the sealing assembly 100. After installing the sealing assembly 100 to the fluid line 102 by threadably mating the housing 116 with the fitting 104, fluid supply to the pump is shut off and the pump is run to pump fluid through the fluid line 102. The flow of fluid through the fluid line 102 in the direction of arrow A shown in FIGS. 3C-3D urges the plug 124 away from the seat 134 such that fluid may flow through an annular space defined between the plug 124 and the seat 134. In this manner, the plug 124 is moved from the closed position (FIGS. 3A-3B) to an open positon (FIGS. 3C-3D). The axial movement of the plug 124 in the direction of the longitudinal axis 122 may be limited by an optional plug stop (not shown). When the pump starts cavitating (i.e., drawing air instead of fluid), the pump may be shut off. After the pump is shut off, the pressure of the fluid in the pool acts on the face of the plug 124 and urges the plug 124 toward the seat 134. In addition, the elastic restoring energy stored in the tension member 148 pulls the body 146 toward the seat 134 and/or the plug liner 126. The plug 124 seals the fluid line 102, thereby preventing fluid from the pool from flowing back into the fluid line 102. In order to purge any remaining fluid from the fluid line 102, air (such as compressed air or air from a blower) may be blown into the fluid line 102 in the direction of arrow A shown in FIGS. 3C-3D. The force of the air acts on the body 146 of the plug 124, thereby unseating the plug 124 from the seat 134 to allow the remaining fluid and air to be purged from the fluid line 102. Once fluid has been purged, removing the air pressure allows the tension member 148 of the plug 124 to pull the body 146 back into a sealing engagement with the seat 134. In this manner, the sealing assembly 100 acts as a one-way check valve to seal the fluid line 102 and prevent fluid from flowing back into the fluid line 102. An optional cap may be removably secured, such as by a threaded connection, to the first end 118 of the housing 116 once fluid has been purged from the fluid line 102 to further seal the sealing assembly 100.

Figure 6:
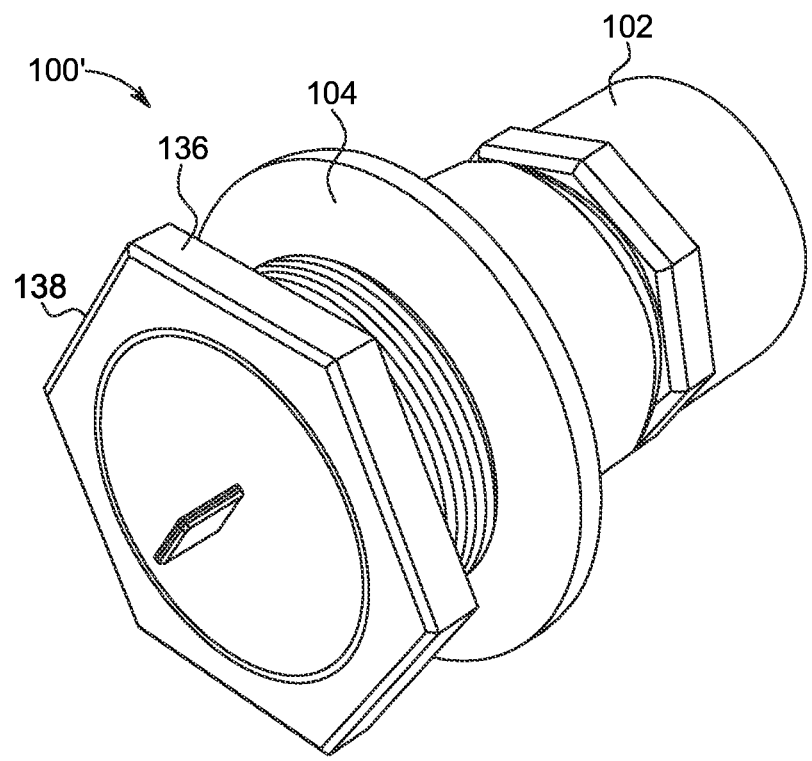
FIG. 6 is a front perspective view of a sealing apparatus of another preferred and non-limiting embodiment or aspect of the present disclosure.
Figure 7:
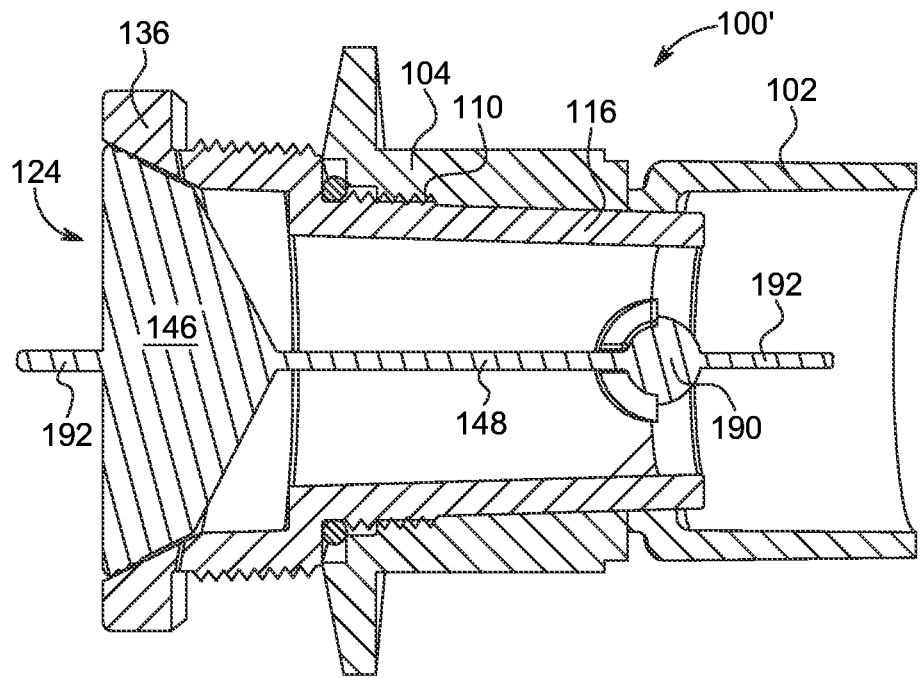
FIG. 7 is a side cross-sectional view of the sealing apparatus shown in FIG. 6 taken along a longitudinal centerline.

With reference to FIGS. 6-7, a sealing apparatus 100' is shown in accordance with another embodiment or aspect of the present disclosure. The components of the sealing apparatus 100' shown in FIGS. 6-7 are substantially similar to the components of the sealing apparatus 100 described herein with reference to FIGS. 1-5. Reference numerals in FIGS. 6-7 are used to illustrate identical components of the corresponding reference numerals in FIGS. 1-5. Only the relative differences between the sealing apparatus 100 shown in FIGS. 1-5 and the sealing apparatus 100' shown in FIGS. 6-7 are discussed hereinafter.

The sealing apparatus 100' in FIGS. 6-7 has a substantially similar structure to the sealing apparatus 100 described with reference to FIGS. 1-5, with the exception that the sealing apparatus 100' in FIGS. 6-7 has a flange 136 having a shape configured to facilitate connection of the housing 116 to the fluid line 102. Specifically, the flange 136 may have a hexagonal or other polygonal shape configured for interfacing with a connection tool, such as a wrench, to rotate the housing 116 in order to threadably engage the housing with the fluid line 102 by way of threads 137.

Figure 8A:
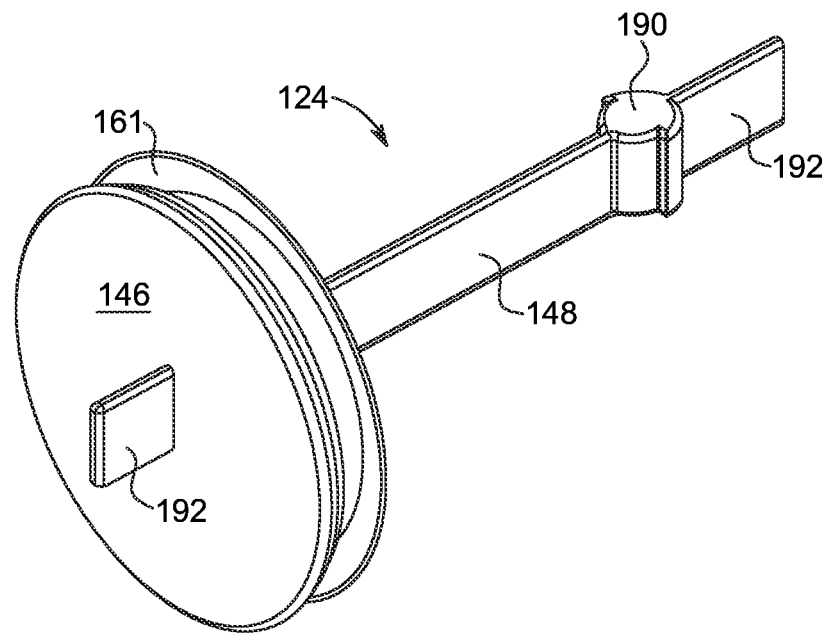
FIG. 8A is a front perspective view of a plug of the sealing apparatus shown in FIG. 7.
Figure 8B:
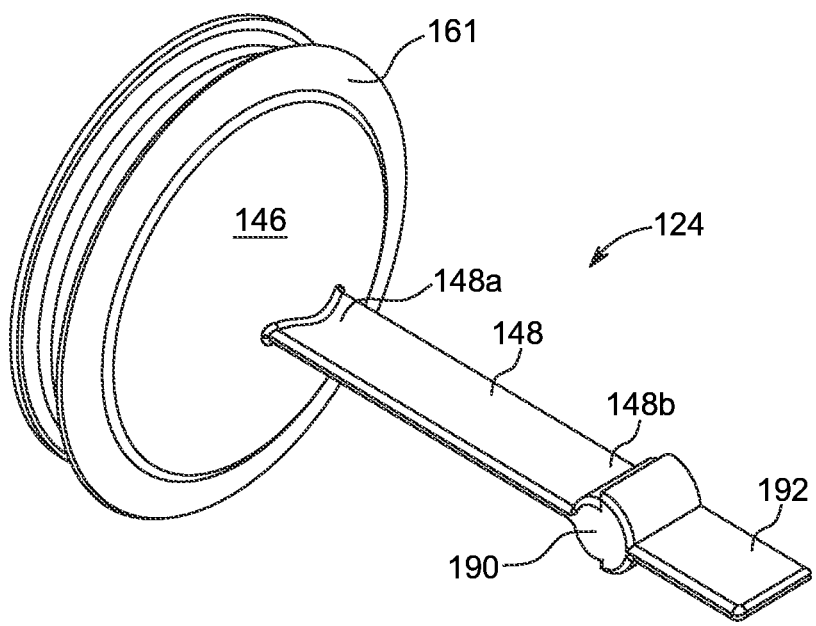
FIG. 8B is a rear perspective view of the plug shown in FIG. 8A.
Figure 9:
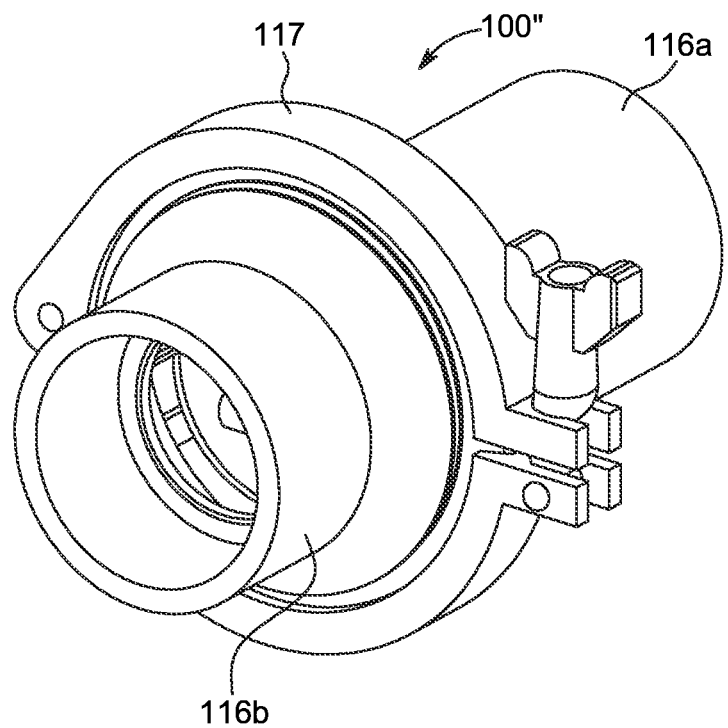
FIG. 9 is a front perspective view of a sealing apparatus of another preferred and non-limiting embodiment or aspect of the present disclosure.
Figure 10:
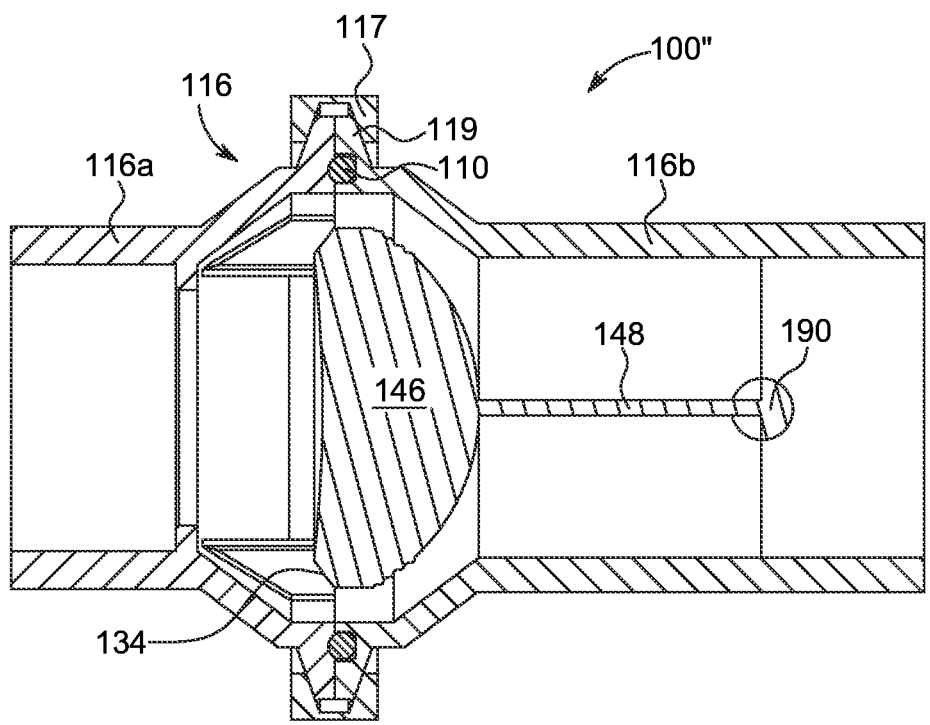
FIG. 10 is a side cross-sectional view of the sealing apparatus shown in FIG. 9 taken along a longitudinal centerline.
Figure 11A:
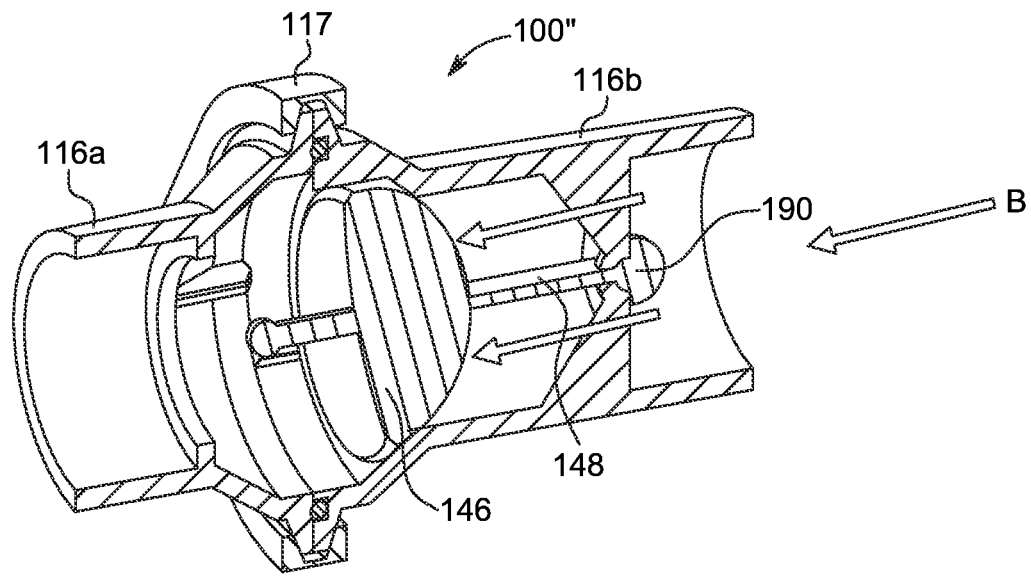
FIG. 11A is a perspective cross-sectional view of the sealing apparatus shown in FIG. 10 showing the sealing apparatus in a closed position.
Figure 11B:
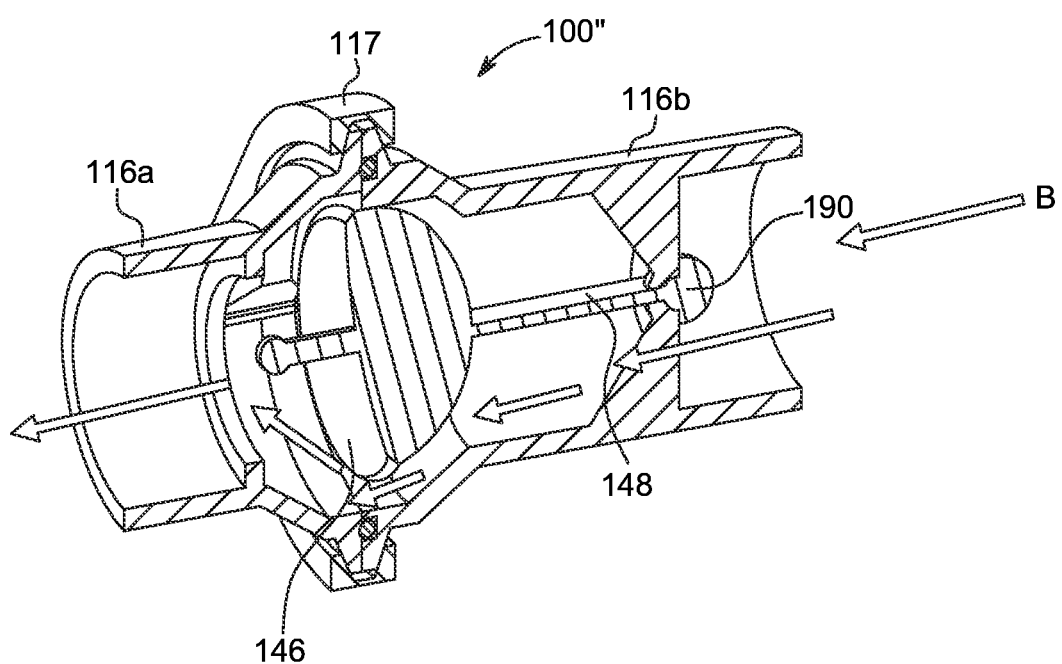
FIG. 11B is a perspective cross-sectional view of the sealing apparatus shown in FIG. 10 showing the sealing apparatus in an open position.

Furthermore, as shown in FIGS. 7-8B, the plug 124 may have at least one gripping element 192 that is configured for being gripped by a user during installation and/or removal of the plug 124 to and from the housing 116. In some examples, the plug 124 may have at least one gripping element 192 on the body 146 of the plug 124 and at least one gripping element 192 on the tail 190 of the plug 124. The gripping element 192 may be formed as a projection that has a first end attached to the body 146 and/or the tail 190 and a second end extending away from the body 146 and/or the tail 190. The gripping element 192 may be monolithically formed with the body 146 and/or the tail 190, or it may be removably or non-removably attached to the body 146 and/or the tail 190. The gripping element 192 is configured to allow the user to grip the plug 124 and pull the tension member 148 during installation and removal of the plug 124 on the housing 116.

With reference to FIGS. 8A-8B, the body 146 of the plug 124 may have at least one lip seal 161. In some examples, the at least one lip seal 161 may be formed as a sealing ring that extends around the circumference of the body 146 of the plug 124. The at least one lip seal 161 may be formed as a deflectable protrusion that extends radially outward from the body 146 of the plug 124. The at least one lip seal 161 is deflectable from a first, undeflected position, such as shown in FIGS. 8A-8B, and a second, deflected position, such as when the plug 124 is installed in the housing 116 and is in a closed position (shown in FIG. 7). The at least one lip seal 161 desirably extends continuously around the entire circumference of the body 146 of the plug 124. In some examples, the at least one lip seal 161 may be monolithically formed with the body 146 of the plug 124. In other examples, the at least one lip seal 161 may be formed separately and connected to the body 146. For example, the at least one lip seal 161 may be fitted into a circumferential groove formed on the body 146. The at least one lip seal 161 is configured to engage the seat 134 on the housing 116 such that a water-tight seal is formed around the circumference of the plug 124 at the interface between the at least one lip seal 161 and the seat 134 on the housing 116.

With reference to FIGS. 9-11B, a sealing apparatus 100" is shown in accordance with another embodiment or aspect of the present disclosure. The components of the sealing apparatus 100" shown in FIGS. 9-11B are substantially similar to the components of the sealing apparatus 100 described herein with reference to FIGS. 1-5. Reference numerals in FIGS. 9-11B are used to illustrate identical components of the corresponding reference numerals in FIGS. 1-5. Only the relative differences between the sealing apparatus 100 shown in FIGS. 1-5 and the sealing apparatus 100" shown in FIGS. 9-11B are discussed hereinafter.

Whereas the sealing apparatus 100 shown in FIGS. 1-5 is configured to be installed at a terminal end of a fluid line, such as at an end of a fluid line opening into a swimming pool, the sealing apparatus 100" is configured for use as an in-line check valve. The sealing assembly 100" has a housing 116 having a first portion 116a and a second portion 116b removably joined together by a clamp 117. The first and second portions 116a, 116b may have a flared end 119 that is configured to fit inside the clamp 117 to prevent the housing 116 from separating axially. In other examples, the first and second portions 116a, 116b may be welded together, or be adhesively connected together. Terminal ends of the first and second portions 116a, 116b opposite the clamp 117 are configured for connecting to pipe sections (not shown) such that the sealing assembly 100" is disposed in-line between adjoining pipe sections.

The plug 124 is formed as a resiliently elastic body that is inserted into the interior of the housing 116 for sealably interfacing with the seat 134. The plug 124 is movable between a first, closed position (FIG. 11A), where the plug 124 seals the interior of the housing 116 and prevents fluid from passing therethrough, and a second, open position, where the plug 124 is disengaged from the seat 134 to allow fluid to flow through the housing 116 in the direction of arrow B (shown in FIG. 11B). In various aspects, the plug 124 may be made from an elastomeric material, such as rubber. The composition of the elastomeric material of the plug 124 may be formulated to be chemically resistant to a variety of fluids, such as water, oil, hydraulic fluid, various gases, and any other liquid or gas. The plug 124 has a substantially conical body 146 and a tension member 148 extending from the body 146. The shape of the body 146 desirably corresponds to the shape of the seat 134 such that the plug 124 may be in surface-to-surface contact with the seat 134 when the plug 124 is in the closed position, as discussed herein.

Figure 12:
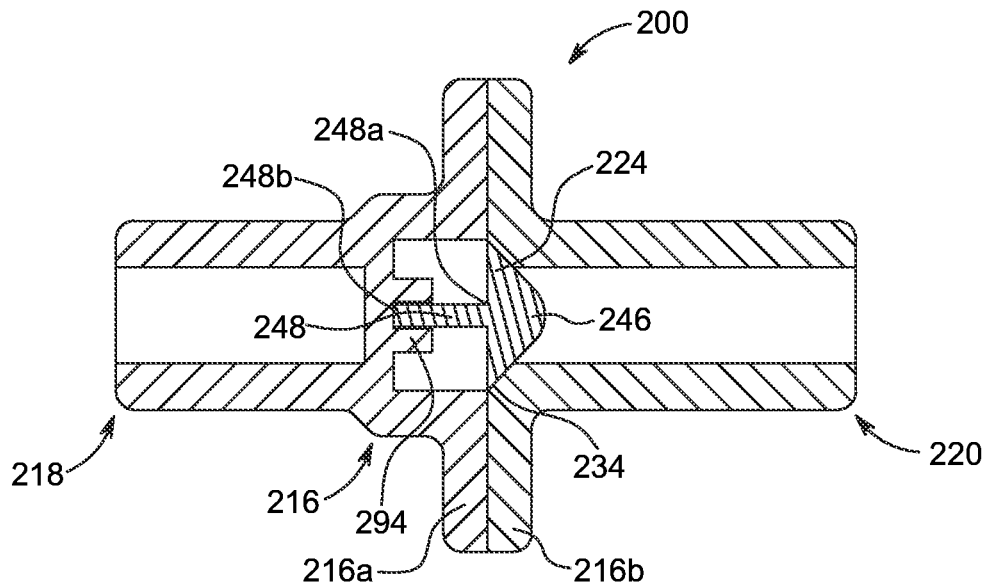
FIG. 12 is a side cross-sectional view of a sealing apparatus of another preferred and non-limiting embodiment or aspect of the present disclosure.
Figure 13:
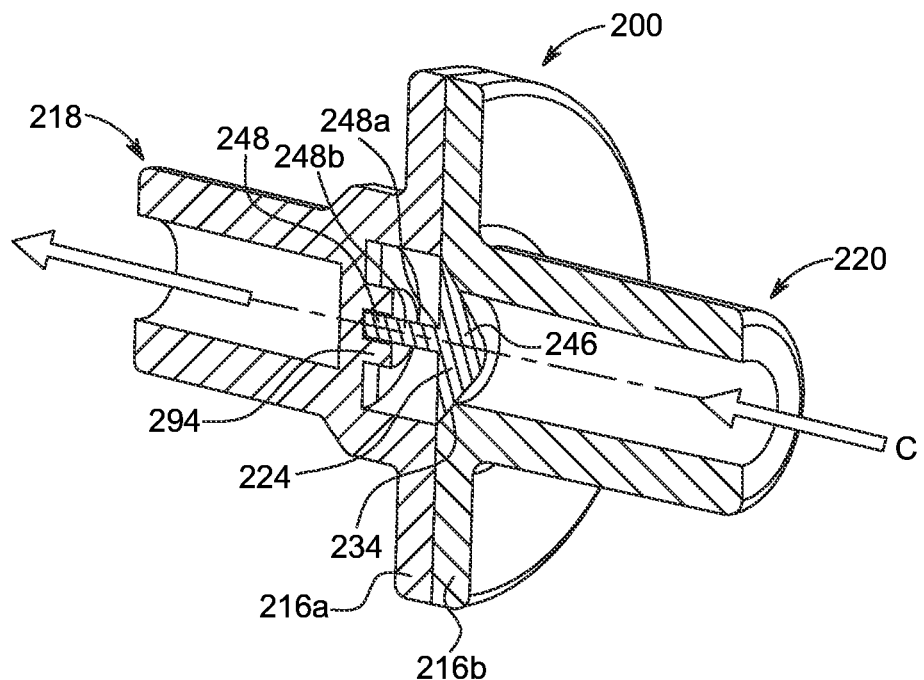
FIG. 13 is a perspective cross-sectional view of the sealing apparatus shown in FIG. 12.

With reference to FIGS. 12-13, a sealing assembly 200 is shown in accordance with another preferred and non-limiting example. The sealing assembly 200 is configured for use as an in-line check valve. The sealing assembly 200 has a housing 216 having a first portion 216a and a second portion 216b removably or non-removably joined together. For example, the first and second portions 216a, 216b may be permanently joined together by welding or adhesive. In other examples, the first and second portions 216a, 216b may be removably joined together, such as with a clamp 117 shown in FIGS. 9-10. Terminal ends of the first and second portions 216a, 216b are configured for connecting to pipe sections (not shown) such that the sealing assembly 200 is disposed in-line between adjoining pipe sections.

The housing 116 has a generally circular cross-section with a hollow interior between a first end 218 and a second end 220 extending along a longitudinal axis 222. The housing 216 receives a plug 224 to seal the housing interior between the first end 218 and the second end 220.

The plug 224 is seated against a seat 234 of one of the first portion 216a and the second portion 216b. Similar to the plug 124 discussed herein with reference to FIGS. 1-5, the plug 224 is formed as a resiliently elastic body that is inserted into the interior of the housing 216 for sealably interfacing with the seat 234. The plug 224 is movable between a first, closed position (FIGS. 12-13), where the plug 224 seals the interior of the housing 216 and prevents fluid from passing therethrough, and a second, open position, where the plug 224 is disengaged from the seat 234 to allow fluid to flow through the housing 216. In various aspects, the plug 224 may be made from an elastomeric material, such as rubber. The composition of the elastomeric material of the plug 224 may be formulated to be chemically resistant to a variety of fluids, such as water, oil, hydraulic fluid, various gases, and any other liquid or gas. The plug 224 has a substantially conical body 246 and a compression member 248 extending from the body 246. The shape of the body 246 desirably corresponds to the shape of the seat 234 such that the plug 224 may be in surface-to-surface contact with the seat 234 when the plug 224 is in the closed position.

The compression member 248 has a first end 248a connected to the body 246 of the plug 224 and a second end 248b extending from the first end 248a along a longitudinal axis of the body 246 of the plug 224. The second end 248b is connected to the housing 216, such as by being received inside a receiver 294 extending across the interior of the housing 216. The plug 224 may be pre-loaded such that the plug 224 is biased in a normally closed position. In this manner, a watertight seal is provided at the interface between the plug 224 and the housing 216 to prevent water from flowing back into the fluid line through the housing 216.

The flow of fluid through the housing 226 in the direction of arrow C shown in FIGS. 12-13 urges the plug 224 away from the seat 234 such that fluid may flow through an annular space defined between the plug 224 and the seat 234. The body 246 of the plug 224 is forced away from the seat 234 by the flowing fluid, thereby compressing the compression member 248. Once fluid flow is reduced to a point where the restoring force of the compression member 248 is greater than the force of the fluid on the body 246 of the plug 224, the compression member 248 "pushes" the body 246 back into a sealing engagement with the seat 234. In this manner, the sealing assembly 200 acts as a one-way check valve to seal the fluid line and prevent fluid from flowing back into the fluid line.

Figure 16A:
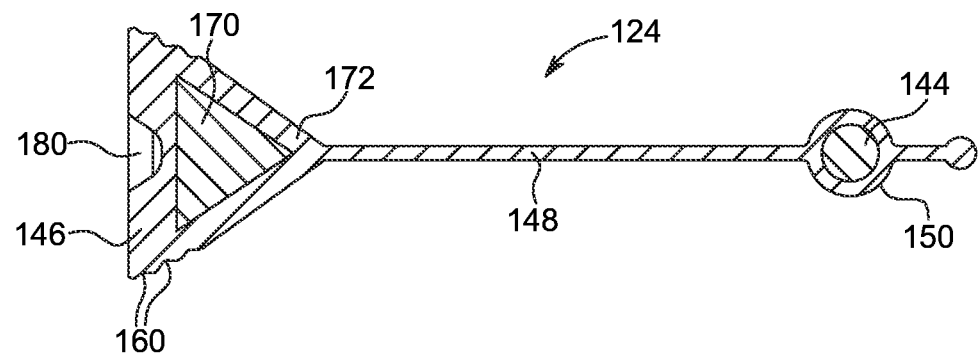
FIG. 16A is a side cross-sectional view of a plug for use with a sealing apparatus in accordance with one preferred and non-limiting embodiment or aspect of the present disclosure.
Figure 16B:
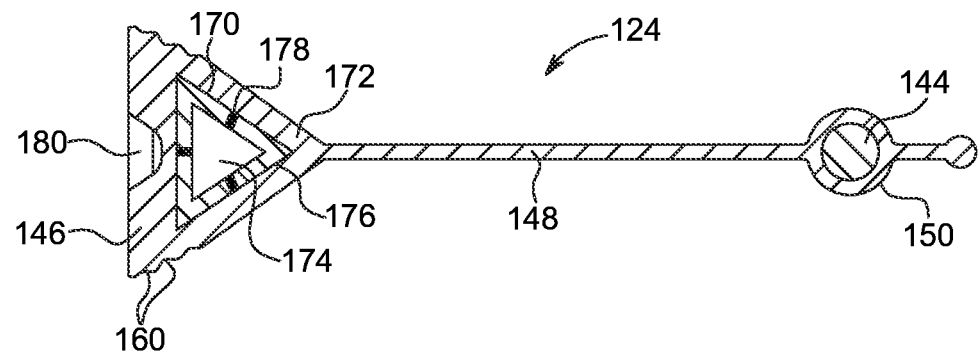
FIG. 16B is a side cross-sectional view of a plug for use with a sealing apparatus in accordance with another preferred and non-limiting embodiment or aspect of the present disclosure.

With reference to FIGS. 16A-16B, the plug 124 is shown in accordance with another aspect of the present disclosure. The plug 124 is formed as a resiliently elastic body that is configured to be inserted into the interior of the housing 116 (shown in FIG. 1) for sealably interfacing with the plug liner and/or the seat 134 (shown in FIG. 1). The plug 124 has a substantially conical body 146 and a tension member 148 extending from the body 146. The shape of the body 146 desirably corresponds to the shape of the plug liner and/or the seat 134 such that the plug 124 may be in surface-to-surface contact with the plug liner and/or the seat 134. The tension member 148 terminates in a receiver 150 that is shaped to receive a pin 144. In some aspects, the receiver 150 may be a substantially circular opening that is configured to receive the pin 144 therethrough. The plug 124 is configured to be installed in the interior of the housing 116 (shown in FIG. 1) such that the body 146 is seated against the conical portion 132 of the housing 116 and the tension member 148 is connected to the recess 140 by way of the pin 144. In this manner, a watertight seal is provided at the interface between the plug 124 and the housing 116 to prevent water from flowing back into the fluid line 102 through the housing 116.

With continued reference to FIGS. 16A-16B, the plug 124 may be made from a plurality of components assembled or joined together to form the plug 124. In some aspects, the plug 124 may have a core 170 at least partially enveloped by a cover 172. The core 170 may be solid, such as shown in FIG. 16A, or hollow, such as shown in FIG. 16B. With reference to FIG. 16A, the core 170 may be a solid, one-piece or multi-piece member formed from plastic, metal, hard rubber, or other material that is more rigid than the elastomeric cover 172. With reference to FIG. 16B, the core 170 may be a hollow, one-piece or multi-piece member having at least one hollow interior cavity 174. In one example, the core 170 may have a skeleton structure 176, optionally having one or more openings 178. The skeleton structure 176 surrounds the hollow interior cavity 174. In other aspects, the hollow interior cavity 174 may have one or more struts (not shown) extending across the interior cavity between portions of the inner wall of the skeleton structure 176.

In either of the aspects shown in FIGS. 16A-16B, the core 170 is at least partially enveloped or surrounded by the cover 172. Desirably, the cover 172 circumscribes the body of the core 170 to form a sealing body that engages against an inner sidewall of the fluid conduit, such as the seat 134. In some examples, the cover 172 may completely cover an exterior surface of the core 170. In other examples, the cover 172 may have a plurality of cover portions, such as cover rings, that are spaced apart from one another along the core 170. The cover 172 may have a uniform or non-uniform thickness. In some examples, the cover 172 may be made from an elastomeric material that is different from the material from which the core 170 is made. Desirably, the elastomeric cover 172 is made from a material with a higher elasticity compared to the material of the core 170 to allow the outer surface of the cover 172 to conform to the seat 134, thereby forming a fluid-tight seal. In some aspects, both the cover 172 and the seat 134 may be made from elastomeric materials, such as rubber, where the cover 172 has higher elasticity compared to the core 170. In other aspects, the cover 172 may be made from an elastomeric material, while the core 170 is made from a rigid material, such as plastic or metal. The cover 172 may be removably or non-removably attached to the core 170, such as by molding, adhesion, or friction fit. In some aspects, the cover 172 may be co-molded with the core 170. The cover 172 may be made from the same or different material as the tension member 148.

With continued reference to FIGS. 16A-16B, an end of the plug 124 opposite to the attachment point of the tension member 148 to the plug body 146 may have at least one recess 180. In some aspects, the recess 180 provides an increased surface area against which fluid may act upon to push the plug body 146 in a direction opposite to a normal direction of fluid flow through the conduit. In this manner, the plug 124 may have improved one-way sealing properties, whereby the hydraulic force of the fluid acting on the face of the plug 124 further urges the plug 124 against the plug liner and/or the seat 134.

With continued reference to FIGS. 16A-16B, the body 146 of the plug 124 has one or more sealing elements 160. In some aspects, the one or more sealing elements 160 may be formed as one or more sealing rings that extend around the circumference of the body 146 of the plug 124. The one or more sealing elements 160 may be spaced apart longitudinally at equal or unequal intervals. In some aspects, the one or more sealing elements 160 may be monolithically formed with the body 146 of the plug 124. In other aspects, the one or more sealing elements 160 may be formed separately and connected to the body 146. For example, the one or more sealing elements 160 may be fitted into a circumferential groove formed on the body 146. The one or more sealing elements 160 are configured to engage the seat 134 on the housing 116 such that a water-tight seal is formed around the circumference of the plug 124 at the interface between the one or more sealing elements 160 and the seat 134 on the housing 116.

While various aspects or embodiments of the sealing apparatus 100 have been described with specific use directed to swimming pools, hot tubs, and/or spas, it should be noted that the sealing apparatus 100 may be configured for use in various other settings. For example, the sealing apparatus 100 may be configured for use in any fluid system where one-way flow control is desired, such as in a food service, petrochemical, or other industrial application. In this manner, the sealing apparatus 100 may function as a one-way check valve that is installed inline or at a terminal end of a fluid conduit. The sealing apparatus 100 may be used in various fields of endeavor.

While specific aspects or embodiments of various examples of a sealing assembly have been described in detail, it will be appreciated by those skilled in the art that various modifications and alternatives to those details could be developed in light of the overall teachings of the disclosure. The presently preferred and non-limiting aspects or embodiments described herein are meant to be illustrative only and not limiting as to the scope of the invention which is to be given the full breadth of the appended claims and any and all equivalents thereof.

The invention claimed is:

1. A sealing assembly for controlling a flow of fluid through a fluid line, the sealing assembly comprising:
   a housing having a first end opposite a second end with a hollow interior extending therebetween;
   an elastically resilient plug disposed within the hollow interior, the plug having a body engagable with a seat within the housing and a tension member having a first end connected to the body and a second end connected to the housing,
   wherein the tension member is pre-loaded in tension to urge the body of the plug against the seat to seal the hollow interior of the housing.

2. The sealing assembly of claim 1, wherein the housing comprises a flange that protrudes radially outward from the housing at the first end of the housing.

3. The sealing assembly of claim 2, wherein the flange comprises one or more gripping members to facilitate handling of the housing during connection of the housing to the fluid line.

4. The sealing assembly of claim 2, wherein the flange comprises one or more threads to threadably interface with at least a portion of the fluid line to removably connect the housing to the fluid line.

5. The sealing assembly of claim 1, wherein at least one of the body of the plug and the seat have a conical shape.

6. The sealing assembly of claim 1, wherein the body is movable away from the seat when the plug is acted upon by a fluid pressure greater than a pre-load force of the tension member.

7. The sealing assembly of claim 1, wherein the plug is made from an elastomeric material.

8. The sealing assembly of claim 1, wherein the second end of the tension member has a bulbous tail that is received in a slot between a pair of substantially parallel bars extending across the hollow interior of the housing.

9. The sealing assembly of claim 8, wherein the plug has at least one gripping element protruding from at least one of the body and the bulbous tail.

10. The sealing assembly of claim 1, wherein the plug comprises a core and a cover at least partially surrounding the core.

11. The sealing assembly of claim 10, wherein the core is hollow or solid.

12. The sealing assembly of claim 10, wherein the cover completely envelops the core.

13. A one-way check valve comprising:
    a housing having a hollow interior;
    an elastomeric plug sealing the hollow interior of the housing, the plug having a body engaged with a seat within the housing and a pre-loaded tension member having a first end connected to the body and a second end connected to the housing,
    wherein at least one of the body of the plug and the seat have a conical shape.

14. The one-way check valve of claim 13, wherein the housing comprises a flange that protrudes radially outward from the housing at the first end of the housing.

15. The one-way check valve of claim 14, wherein the flange comprises one or more gripping members to facilitate handling of the housing during connection of the housing to the fluid line.

16. The one-way check valve of claim 14, wherein the flange comprises one or more threads to threadably interface with at least a portion of the fluid line to removably connect the housing to the fluid line.

17. The one-way check valve of claim 13, wherein the second end of the tension member has a bulbous tail that is received in a slot between a pair of substantially parallel bars extending across the hollow interior of the housing.

18. The one-way check valve of claim 13, wherein the plug is movable away from the seat when the plug is acted upon by a fluid pressure greater than a pre-load force of the tension member.

19. A sealing assembly for controlling a flow of fluid through a fluid line, the sealing assembly comprising:
    a housing having a first end opposite a second end with a hollow interior extending therebetween;
    an elastomeric plug disposed within the hollow interior, the plug having a body engagable with a seat within the housing and an elastic compression member having a first end connected to the body and a second end connected to the housing,
    wherein the compression member is pre-loaded in compression to urge the body of the plug against the seat to seal the hollow interior of the housing, and
    wherein the plug has a substantially conical body shaped to correspond to a shape of the seat such that the plug and the seat are in a surface-to-surface contact.

* * * * *